United States Patent
Yang et al.

(10) Patent No.: US 7,129,201 B2
(45) Date of Patent: Oct. 31, 2006

(54) AQUEOUS-AQUEOUS EMULSIONS COMPRISING A DISPERSED PHASE AND A CONTINUOUS SURFACTANT PHASE WITH ROD-LIKE SURFACTANTS

(75) Inventors: Lin Yang, Fort Lee, NJ (US); Rajesh Patel, Lyndhurst, NJ (US); Kavssery Parameswaran Ananthapadmanabhan, Highland Mills, NJ (US); Judith Lynne Kerschner, Hawthorne, NJ (US)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 228 days.

(21) Appl. No.: 10/643,173

(22) Filed: Aug. 18, 2003

(65) Prior Publication Data
US 2005/0039253 A1 Feb. 24, 2005

(51) Int. Cl.
*C11D 17/00* (2006.01)

(52) U.S. Cl. ............ 510/417; 510/428; 510/470
(58) Field of Classification Search ........... 510/417, 510/424, 426, 428, 433, 432, 470, 405
See application file for complete search history.

(56) References Cited

U.S. PATENT DOCUMENTS

| | | | | |
|---|---|---|---|---|
| 5,785,979 | A | * | 7/1998 | Wells ............ 424/401 |
| 5,922,664 | A | * | 7/1999 | Cao et al. ............ 510/340 |
| 6,429,177 | B1 | | 8/2002 | Williams et al. |
| 6,531,442 | B1 | * | 3/2003 | Durbut et al. ............ 510/421 |
| 6,534,456 | B1 | * | 3/2003 | Hayward et al. ............ 510/130 |
| 6,797,683 | B1 | * | 9/2004 | Shana'a et al. ............ 510/370 |
| 2002/0055461 | A1 | | 5/2002 | Jin et al. |
| 2004/0033914 | A1 | | 2/2004 | Patel et al. |
| 2004/0038837 | A1 | | 2/2004 | Pereira et al. |

* cited by examiner

*Primary Examiner*—Gregory Webb
(74) *Attorney, Agent, or Firm*—Ronald A. Koatz

(57) ABSTRACT

The invention relates to stable aqueous-aqueous emulsions defined by a dispersed phase having molecule(s) meeting special criteria and continuous phase having surfactant or surfactant system with micelles in rod-like shapes.

12 Claims, 8 Drawing Sheets

(a)

(b)

Phase diagram of SLES/CAPB (2:1) – MD 180 – Water at room temperature. (a) The formulation points that were examined in this study. The dotted line is the boundary between the one-layer product and the two-layer product; (b) The phase boundaries between difference phases.

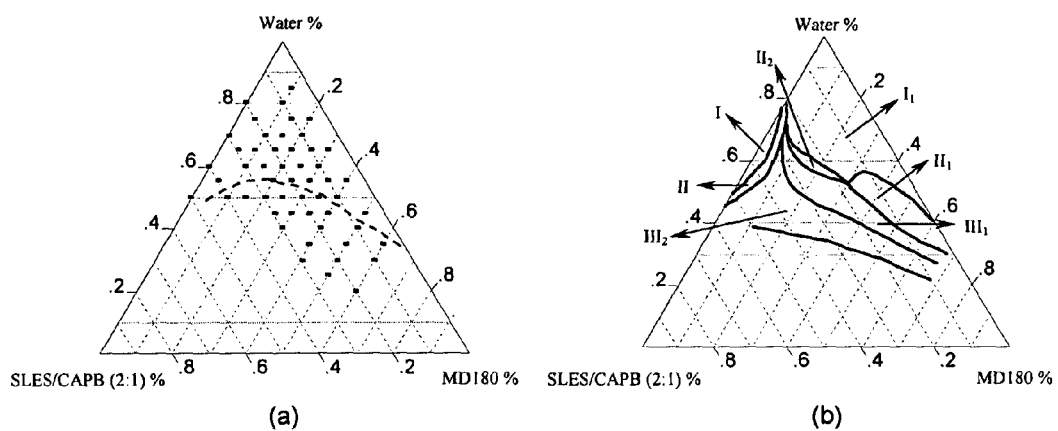
Figure 1: Phase diagram of SLES/CAPB (2:1) - MD 180 – Water at room temperature. (a) The formulation points that were examined in this study. The dotted line is the boundary between the one-layer product and the two-layer product; (b) The phase boundaries between difference phases.

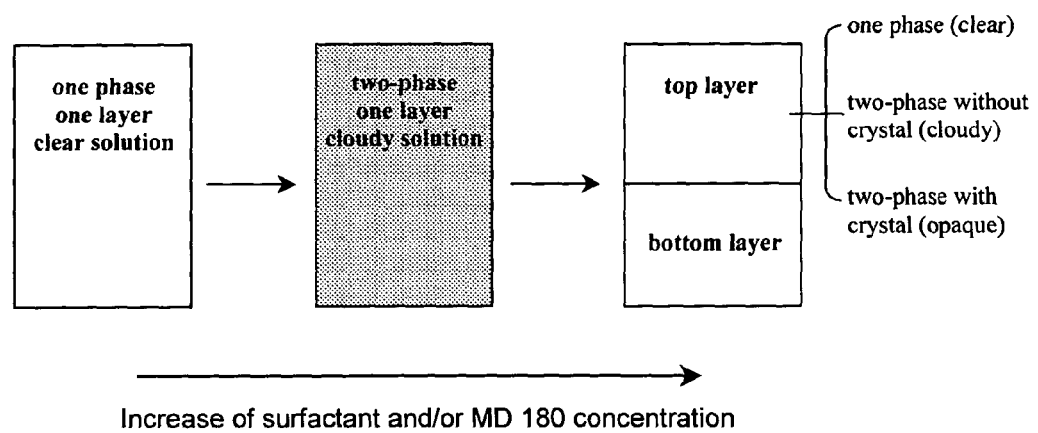
Figure 2. Schematics of the product appearance upon the increase of the surfactant and/or MD 180 concentration.

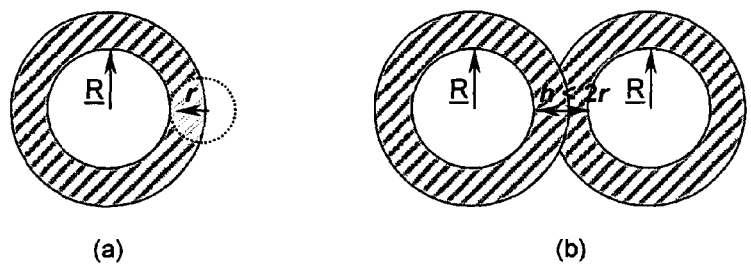

Figure 3: Schematics of the depletion flocculation in a system containing small particles of radius $r$ and large particles of radius $R$. (a). The depletion zone of width $r$ around a large particle of radius $R$ that the center of a small particle of radius $r$ can not penetrate into. (b). The small particles will be excluded from the gap of $h < 2r$ between two large particles.

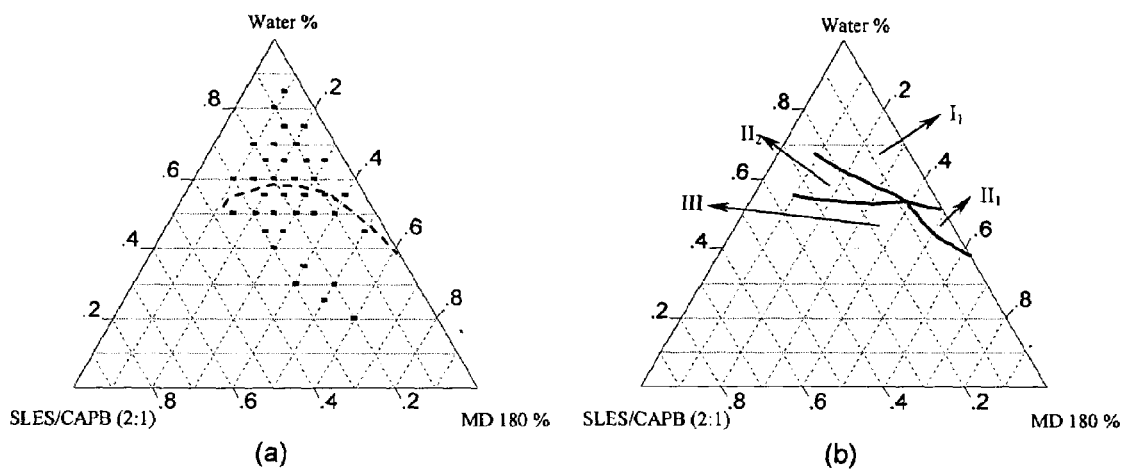
Figure 4: Phase diagram of SLES/CAPB (2:1) - MD 180 – Water with 1% NaCl at room temperature. (a) The formulation points that were examined in this study. The dotted line is the boundary between the one-layer product and the two-layer product; (b) The phase boundaries between difference phases.

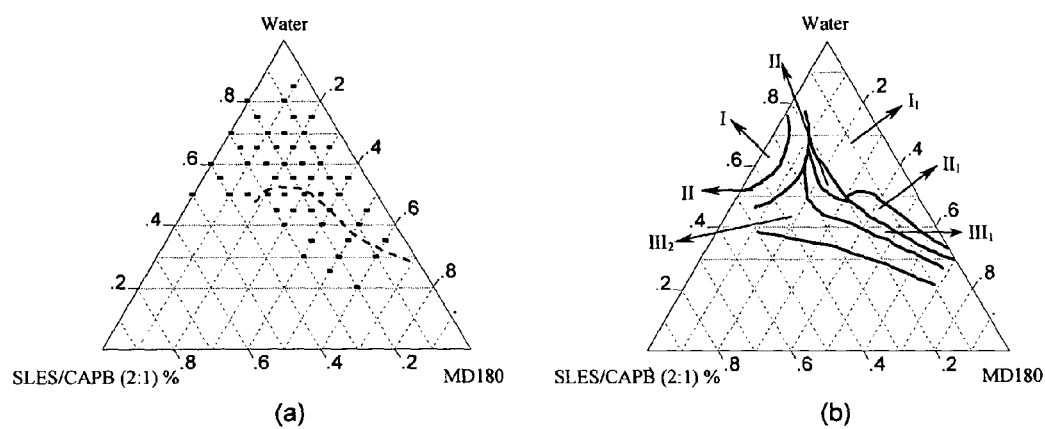
Figure 5: Phase diagram of SLES/CAPB (2:1) - MD 180 – Water with 5% glycerol at room temperature. (a) The formulation points that were examined in this study. The dotted line is the boundary between the one-layer product and the two-layer product; (b) The phase boundaries between difference phases.

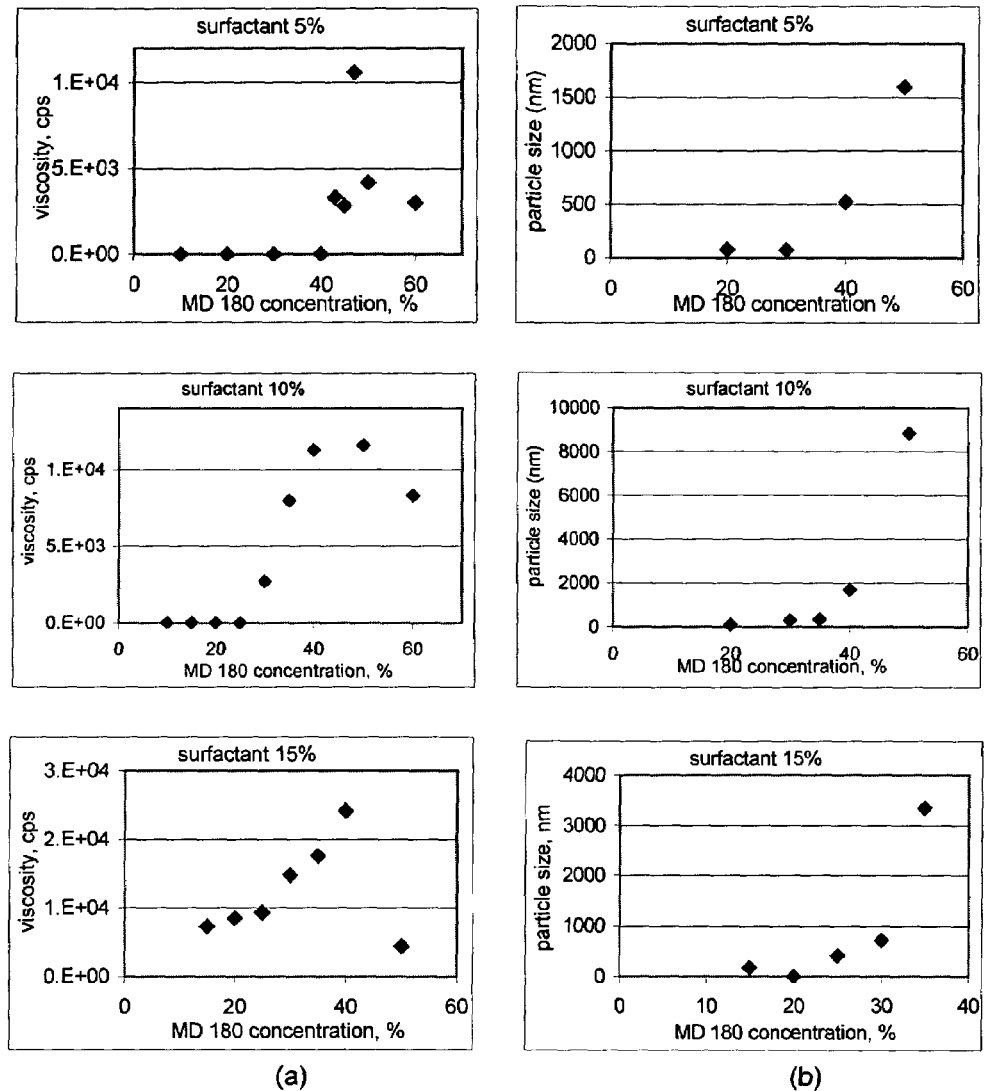
Figure 6: Viscosity and particle size for SLES/CAPB (2:1) – MD 180 – water system at surfactant concentration equals to 5%, 10% and 15%. Column (a). Viscosity at shear rate 10 s$^{-1}$ vs. the MD 180 concentration; Column (b). Particle size vs. the MD 180 concentration.

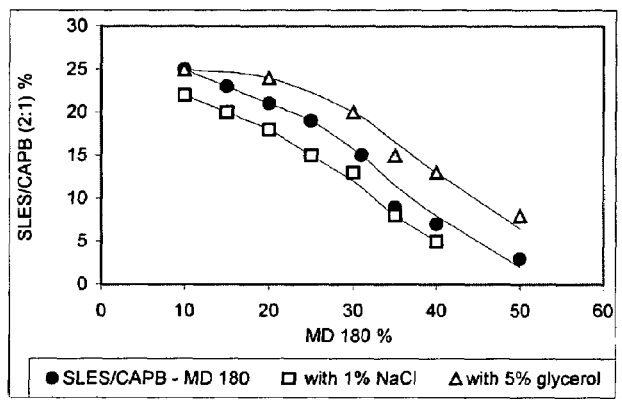
Figure 7. Surfactant concentration at the phase boundary vs. the MD 180 concentration at the phase boundary for SLES/CAPB (2:1) – MD 180 – water formulation, SLES/CAPB (2:1) – MD 180 – water with 1% NaCl, SLES/CAPB (2:1) – MD 180 – water with 5% glycerol

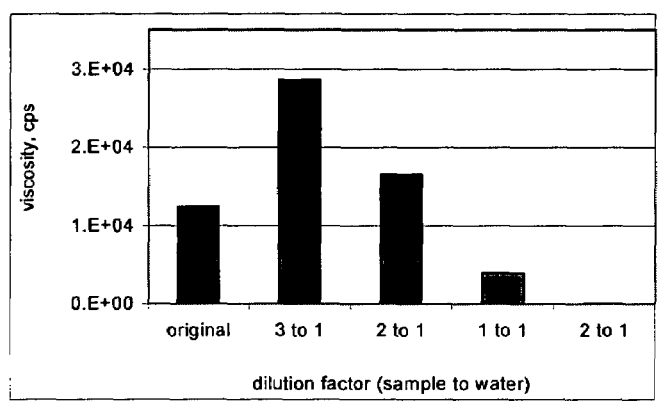
Figure 8. Viscosity changes (at shear rate 10 $S^{-1}$) of the formulation SLES/CAPB (2:1) 20%, MD 180 50% upon dilution with water.

AQUEOUS-AQUEOUS EMULSIONS COMPRISING A DISPERSED PHASE AND A CONTINUOUS SURFACTANT PHASE WITH ROD-LIKE SURFACTANTS

FIELD OF THE INVENTION

The present invention relates to liquid compositions and in particular to liquid compositions comprising stable aqueous-aqueous emulsions. In particular, the emulsions are aqueous-aqueous emulsions formed by the combination of molecules meeting defined criteria (e.g., water solubility of at least certain amount; minimum and maximum MW), added in solid form or as an aqueous solution, with an aqueous surfactant solution wherein the surfactant or surfactants in the solution are capable of forming rod-like micelles and the ability to do so is defined by surfactant parameter of the surfactant and/or surfactant system (e.g., one or more surfactants may form a single species of micelle). More specifically, the invention is concerned with specific regions of the dispersed molecule (e.g., saccharides such as maltodextrin)-water-surfactant system which are stable emulsions formed when rod-like surfactants of the continuous surfactant phase (through what is believed to be a process wherein molecules of the dispersed phase are depleted to form separation), envelop the dispersed, molecule comprising phase (i.e., molecule of defined solubility and MW) to form said stable emulsion, even in the absence of emulsifier between the two aqueous phases. A stable emulsion generally refers to the resistance of emulsions to the coalescence of their droplets.

BACKGROUND OF THE INVENTION

Conventional emulsions are typically formed when a liquid phase is dispersed in another immiscible liquid phase, e.g., oil in water or water in oil, and the dispersion is stabilized against coalescence by a steric and/or electrical barrier (e.g., surfactant) at the interface between the dispersed phase and the continuous phase.

Emulsions of the subject invention, on the other hand, are so-called aqueous-aqueous emulsions in which both the dispersed phase and the continuous phase are aqueous in nature. Such aqueous-aqueous emulsions do not have the "heavy oil" feel associated with conventional emulsions formed by oil and water. Further, since the dispersed phase is aqueous, highly water soluble benefit agents (e.g., glycerin, proteins) can be integrated or encapsulated in the dispersed phase offering potential of high delivery efficiency to skin or other substrate from a wash off product. Because the dispersed phase is typically and preferably poor in surfactant (for example, less than 5% by wt.), bioactive agents such as proteins also have a better chance to preserve their native structures in such aqueous-aqueous emulsions.

U.S. Pat. No. 6,429,177 to Williams et al. discloses aqueous-aqueous biphasic compositions comprising surfactant, thickener (e.g., hydrophobically modified polyethylene glycols such as PEG (160) sorbitan triisostearate), polyalkylene glycol and chelating salt to induce phase separation. This reference discloses biphasic liquids rather than stable aqueous-aqueous emulsions of the invention and further fails to define how the stable emulsion of the invention would be formed or what they are made of.

Applicants have also filed two co-pending applications entitled "Biphasic Composition Induced by Polydextrose" to Patel et al.; and "Biphasic Composition Induced by Polydextrose and Sucrose" to Pereira et al., both filed on Aug. 14, 2002. These disclose use of polydextrose to induce biphasic liquids and fail to disclose the stable aqueous-aqueous emulsions of the objection. They further fail to disclose how to form such emulsions and what they are made of.

Finally, U.S. patent application Publication No. U.S. 2002/0055461 A1 to Jin et al., published May 9, 2002, discloses a stable polymer aqueous-aqueous emulsion system. This reference requires use of a third charged particle phase that is critical because it coats the dispersed phase and provides an electrical barrier to prevent the coalescence of the dispersed phase. In the subject invention, the disclosed aqueous-aqueous emulsion is formed by surfactant and a molecule (defined by specific water solubility and MW) upon mixing with water and no additional emulsifier is required. The reference fails to teach specific dispersed phase molecule and surfactant or surfactant system of continuous phase of the subject invention.

BRIEF DESCRIPTION OF THE INVENTION

Unexpectedly, applicants have found compositions and processes for making compositions wherein a unique, stable, aqueous-aqueous emulsion region (formed by adding defined molecule, e.g., saccharides, to surfactant system having surfactant of defined properties) is formed. Specifically, applicants have now defined such a region where such stability is found, even in the absence of emulsifier.

More specifically, the compositions of the invention are liquid compositions comprising stable (e.g., the dispersed droplets forming the emulsion resist coalescence), aqueous-aqueous emulsion, wherein said emulsion comprises:
(1) a dispersed aqueous phase comprising a molecule(s) meeting the following criteria:
  (a) water solubility greater than 5%, preferably greater than 10%, more preferably greater than 15% at 25° C.;
  (b) MW>200, preferably >250, more preferably >300 and also MW<200,000, preferably less than 195,000, more preferably <190,000;
(2) a continuous aqueous phase comprising surfactant or surfactants, having micelles in rod-like shape,
  wherein rod-like is defined by a surfactant parameter of surfactant or surfactants forming the micelle, Ns, of about ⅓ to ½, where Ns is defined by the equation:

$Ns = V/(Ia_o)$;

where V=volume of the hydrophobic portion of the surfactant molecule;
  I=the length of the hydrocarbon chains of the surfactant; and
  $a_o$=effective area per head group.

BRIEF DESCRIPTION OF THE FIGURES

FIG. 1A is a ternary phase diagram of SLES/CAPB (2:1)—maltodextrose—water system at room temperature. Points are mixtures (formulations) examined and dotted line is boundary between one-layer and two-layer (bi-phasic) product. FIG. 1B shows phase boundaries of same system used in 1A between different phases.

FIG. 2 is a schematic of product appearance upon increase of surfactant and/or saccharide (MD 180) concentration.

FIG. 3 is a schematic of depletion flocculation in a system with small and large radius particles.

FIG. 4 is phase diagram of SLES/CAPB (2:1)—saccharide (MD 180)—water with 1% NaCl at room temperature. Points are mixtures (formulations) examined in study and dotted lines are the boundary between one and two layers. FIG. 4(b) shows phase boundaries between different phases.

FIG. 5 shows phase diagram of SLES/CAPB (2:1)—MD 180—water with 5% glycerol measured at room temperature. Points are mixtures (formulations) examined in study and dotted lines are the boundary between one and two layers. FIG. 5(b) shows phase boundaries between different phases.

FIG. 6 shows relation of viscosity and particle size in system of invention.

FIG. 7 shows effect of salt and glycerol on phase boundary.

FIG. 8 shows viscosity changes of formulation upon dilution with water.

DETAILED DESCRIPTION OF THE INVENTION

The invention relates to specific compositions which can be defined by certain boundary regions of a ternary diagram plotting (1) water; (2) surfactant; and (3) a third component (for example, specifically defined saccharides or other molecules meeting specific criteria). The region described by the ternary diagram is one where there is achieved a stable, aqueous-aqueous emulsion. While not wishing to be bound by theory, the emulsion is believed to form by mixing the water, surfactant and molecule which initiates a depletion effect whereby contacting the molecule and surfactant leads to formation of a rod-like phase of the surfactant which in turn depletes the molecule and forces the formation of the emulsion (this is referred to as depletion induced phase separation).

The aqueous-aqueous emulsion so-formed can also be defined by the aqueous phases of the emulsion wherein one phase of the emulsion (dispersion phase) is an aqueous phase comprising a molecule defined by specific solubility and molecule weight characteristics; and the dispersed phase is defined by the ability of surfactant or surfactants in the surfactant system to form rod-like micelles and wherein this ability is in turn defined by a surfactant parameter ($N_s$) which defines the shape of the surfactant micelle.

Before the formation of the stable aqueous-aqueous emulsion, the surfactant, water and molecule of defined size and solubility are generally part of an isotropic, single phase (clear) solution. As high concentrations of surfactant and/or molecules (e.g., saccharide, such as maltodextrin) are used, the single phase solution generally will separate into a so-called "biphasic" two phase solution (see FIG. 1A). Typically, such compositions have a bottom layer poor in surfactant and rich in, for example, polysaccharide.

Taking a surfactant mixture of SLES (sodiumlauryl ether sulfate) and CAPB (cocoamidopropylbetaine)/MD 180 (maltodextrin 180)/water as a sample system, the top layer of a two-layer formulation can be clear (for one-phase), cloudy (for two-phase of solutions), or opaque (hexagonal crystal in solution), depending on the phase structures. It can be one phase (a surfactant/MD 180 water solution), or two-phase without liquid crystal (a surfactant rich/MD 180 poor water solution+a surfactant/MD 180 water solution), or two-phase with liquid crystal (a surfactant rich/MD 180 poor water solution+hexagonal phase). The bottom layer will be a surfactant poor, MD 180—rich, single phase solution.

As indicated by the phase diagram shown in FIG. 1(b), SLES/CAPB (2:1)—MD 180—water system exhibits a rich phase behavior. At low surfactant concentration and low MD 180 concentration, one phase region of SLES/CAPB (2:1)+ MD 180 water solution (denoted as $I_1$) exists. As the MD 180 or surfactant concentration increases, phase separation happens. Two two-phase regions exist on the phase diagram, a mixture of a surfactant/MD 180 solution with a MD 180 rich/surfactant poor solution (denoted as $II_1$), or a mixture of a surfactant rich/MD 180 poor solution with a surfactant/ MD 180 solution (denoted as $II_2$). As the surfactant and/or MD 180 concentrations keep on increasing, a three-phase region (denoted as $III_1$), which is a mixture of a surfactant rich/MD 180 poor solution, a surfactant/MD 180 solution and a MD 180 rich/surfactant poor solution, is formed. After that, the increase of MD 180 and/or surfactant concentration leads to another three-phase region ($III_2$), formed by surfactant hexagonal liquid crystal phase, surfactant rich/MD 180 poor phase and a MD 180 rich/surfactant poor phase. It is also noted from the phase diagram that along the SLES/ CAPB (2:1) concentration axis, at the low MD 180 concentration region, there is a one-phase region (denoted as I), which is surfactant hexagonal liquid crystal phase, as well as a two-phase region (denoted as II), which is a mixture of surfactant hexagonal liquid crystal phase and a surfactant water solution. The schematics of the evolution of the phase behavior upon the increase of surfactant and/or MD 180 concentration are shown in FIG. 2.

The area which the subject invention is concerned with (and which is defined by the dispersed layer comprising defined molecule and continuous layer of defined surfactants) are the two-phase regions in FIG. 1(b) defined by $II_1$ and $II_2$.

In the aqueous-aqueous emulsion of the invention, both dispersed and continuous phases are water rich and no other water immiscible solvent is required in the current system. Upon the addition of molecule, e.g., Maltodextrin, into the surfactant water solution, the shape of the surfactant micelle changes from sphere to rod and phase separation happens. The continuous phase formed by rod-like surfactant micelles exhibits a high viscosity where the coalescence of the dispersed phase is greatly reduced and the aqueous/aqueous emulsion is stable.

Without wishing to be bound by theory, the regions defined by $II_1$ and $II_2$ (in the specific example; it should be understood these regions would be different if the specific surfactant system and/or molecule of defined solubility and MW were different that those of the subject example; or if, as discussed below, other molecules such as salts or glycerol are used in forming the emulsion) are believed formed by a this so-called depletion-induced phase separation.

Depletion Flocculation

This depletion-induced phase separation is described in more detail as follows. For a colloidal system containing small particles of radius r and large particles of radius R, phase separation may occur due to the so-called depletion attractive force. A depletion force is induced by the following effects: for a separation of h<2r between two larger particles, small particles of radius rare excluded from the gap between the larger ones, and a concentration gradient of the excluded small particles between the bulk solution and the gap is thus formed. This concentration difference of the small particles will cause an attractive force between the larger particles, equal to the osmotic pressure of the excluded species outside the gap. From the thermodynamics point of view, depletion flocculation is an entropy driven process. As shown in FIG. 3(a), each large colloidal particle has a depletion zone of the radius of the small particle r, that the center of the small particle can not penetrate into. As two large particles approach each other, the depletion zone of these two particles might overlap, and the available volume in the system for the small particle increases, which leads to an increase of the entropy and thus a decrease of the free energy.

It has been found by both theoretical calculation and experimental observation that rod-like colloidal particles are extremely effective in causing depletion flocculation. For instance, if the ratio of the radius of the large particle to that of the small particle is 10:1, around 20% small particles will be required to cause the depletion flocculation if both particles are spherical shape; while only 0.56% small particle will be necessary for depletion flocculation if the system is a sphere and rod mixture. The reason is that, for the same sample volume fraction of spheres and rods, the rotation of the rod-like particles in the 3-D space will lead to a much larger effective depletion zone than that of the spherical particles. Therefore, rod-like micelles will cause depletion induced phase separation at much lower actual volume fraction.

Keeping in mind the example of phase diagram defining a stable aqueous-aqueous emulsion region an a proposed mechanism for formation, as defined above, the application will now define in further detail the emulsion composition.

Dispersed Aqueous Phase

The dispersed aqueous phase uses a molecule or material that will exhibit phase separation from surfactants or surfactant system under the depletion flocculation mechanism proposed above. Such molecules must meet at least the following two criteria.

First, they need be hydrophilic enough to be well compatible with water. Specifically, molecules should have water solubility of >5%, preferably >10%, more preferably >15% as measured at 25° C. Second, the MW of the molecules cannot be too small. If it is too small, depletion will not readily occur and thus phase separation is inhibited. The molecule also cannot be too large or the entanglement of molecular claims will not cause phase separation in macro scale due to high viscosity and slow separation kinetics.

Thus, MW of the molecule should be >200, preferably greater than 250, more preferably >300 and, on the other hand, MW should be <200,000, preferably less than 195,000, more preferably less than 190,000.

Examples of molecules which will separate and disperse in the dispersed aqueous phase are, for example, saccharides, particularly oligosaccharides such as maltodextrins (MW 500–5,000), or Dextrin of MW 70,000, or polyglucose (MW 500–5000). Other examples include polyvinylpyrrilodone (PVP) of MW 7000 and PEG of MW 1000.

Small sugars, for example, sucrose, glucose, sorbitol, or large molecular weight polysaccharides (e.g., Dextran of MW 250,000) would not be expected to work.

Continuous Surfactant Phase

As noted above, formation of aqueous-aqueous emulsion is believed to be by depletion-induced separation. It has been found, by theoretical calculation and experimental observation, that rod-like colloidal particles (e.g., in the continuous phase) are extremely effective in causing depletion flocculation. Therefore, the formation of the rod-like surfactant micelle is critical in the current invented system in order to phase separate to aqueous-aqueous emulsion. The stability of the aqueous-aqueous emulsion is achieved by the inherently high viscosity of the continuous phase containing the rod-like surfactant micelles. Therefore, the criteria of the surfactants that work will be that the said surfactant is able to for a rod-like micelle.

A surfactant parameter ($N_s$) is defined to predict the shape of the surfactant micelle.

$$Ns=V/(Ia_o)$$

where V is the volume of the hydrophobic portion of the surfactant molecule, I is the length of the hydrocarbon chains, and $a_o$ is the effective area per head group. Optimal stability of the different micelle aggregates in aqueous media occurs as follows:

Spherical micelles $Ns=0-\frac{1}{3}$

Cylindrical (rod-like) micelles $Ns=\frac{1}{3}-\frac{1}{2}$

Lamellar micelles $Ns=\frac{1}{2}-1$

For instance, surfactants having two long alkyl chains (larger value of the volume of the hydrophobic portion of the surfactant molecule V) will have larger Ns value and tend to form lamellar micelles. For ionic surfactants, adding electrolyte or increasing the surfactant concentration will lead to a decrease of the effective area per head group (a). Therefore, the shape of the micelle may shift to a shape of less curvature (such as cylindrical or lamellar micelle).

In short, the criteria of the surfactants that may be used to induce formation of an aqueous-aqueous emulsion is that the surfactant is able to form rod-like micelle in aqueous media with or without electrolytes, co-solvents, and/or co-surfactant. A convenient approach to predict the formation of rod-like micelle is by calculating the surfactant parameter Ns as defined above.

Surfactants or surfactant systems (surfactant containing formulation with small additives, co-solvents or co-surfactant) that can not form rod-like micelles will not be able to phase separate into an aqueous-aqueous emulsion upon the addition of defined molecule (e.g., saccharides) through the depletion-induced phase separation. A semi-empirical way to judge whether they will form rod micelles is by calculating the surfactant parameter (Ns) as shown in equation above. Surfactants which have a bulky headgroup (e.g., double headed surfactant or long chain hydrophilic group, such as sulphosuccinimates, salt of monoester of sulphosuccinic acid or half ester, alkyl phenol ethoxylates,) tend to have a larger effective area per headgroup. Therefore (i.e., because the denominator is larger), the surfactant parameter of those surfactants tend to be small ($<\frac{1}{3}$) and the optimal geometry of the surfactant micelles tends to be spherical. Those surfactants with small surfactant parameter (Ns) tend to not cause phase separation.

For surfactants with bulky yet relative short tails, such as those double tails surfactants (e.g., paraffin (alkane) sulphonates, diester of sulphosuccinic acid salt, diester of phosphoric acid), the surfactant parameter (Ns) tends to be big ($>\frac{1}{2}$) and the optimal geometry tends to be lamellar. Those surfactants also tend not to cause phase separation.

Surfactants that do work will be those having surfactant parameter $Ns=\frac{1}{3}-\frac{1}{2}$.

One example of the surfactant is the phase separation of SLES/CAPB+CAPB+MD 180 (See FIG. 1).

Another example of a surfactant system with the required Ns value is the mixture referred to as Almeo blend (containing 43.5% alkyl lauryl sulfate (ALS), 43.5% alkyl lauryl ether sulfate (ALE1S), 8.7% cocomonoethanolamide (CMEA) and 4.3% CMEA 5EO) and cocoaminopropylbetaine (CAPB) in weight ratio of Almeo to CAPB of 4:1. The mixture of surfactant phase may separate in the following composition for example as follows: Almeo/CAPB 4:1 (25%)+MD-180 (8%)+water (67%).

Yet another example of an adequate surfactant is the SLES with saccharide dissolved therein and with no cosurfactant.

Stable Region Characterization

Yet another way to characterize the region where a stable aqueous-aqueous emulsion exists is to measure the particle size in that region. Phase separation is confirmed if the measured particle size is greater than 200 MW nanometer. Rheology measurement can also be carried out to confirm formation of rod-like micelle, which micelles are believed to trigger phase separation as proposed in the phase-separation mechanism. Generally, an increase in viscosity is an indication of formation of rod-like micelles in solution. Phase separation happens by increase of particle size and, as indicated, will occur at concentration range where rod-micelles form.

While not wishing to be bound by theory, it is hypothesized addition of dispersed particle (e.g., saccharide) and decrease of water content in system causes surfactant aggregates to change shape from spherical to rod. The sufficiency of rod-like micelles in causing depletion induced phase separation in turn allows surfactant/saccharide (for example) water mixture to separate into two phases.

Emulsion With Salt

In another embodiment of the invention, salt (e.g., alkali metal chloride) can be added with the surfactant, water and molecule during formation of aqueous-aqueous emulsion.

The phase diagram of SLES/CAPB (2:1)—MD 180—water with 1% NaCl at room temperature is shown in FIG. 4(b). It is found that at low surfactant and/or low saccharide (MD 180) concentration, an isotropic solution phase exists. With the increase of the surfactant and/or saccharide concentration, two two-phase regions are encountered, similar phase diagram for the SLES/CAPB (2:1)—MD 180—water without NaCl. Further increases of the surfactant and/or MD 180 concentration result in the formation of a three-phase region, which is the mixture of the surfactant hexagonal phase, a surfactant rich/MD 180 poor solution, and a surfactant poor/MD 180 rich solution phase.

The discontinuous line in FIG. 4(a) is the boundary that the formulation starts to separate into two layers. For biphasic product of SLES/CAPB—MD 180 with 1% NaCl, the bottom layer is the surfactant poor/MD 180 rich solution. The top layer can be a clear one phase solution (a surfactant+MD 180 water solution), or an opaque two-phase mixture with liquid crystal (a surfactant rich/MD 180 poor water solution+hexagonal phase).

Comparing the phase diagrams of SLES/CAPB—MD 180—water systems with and without NaCl, it is found that the three-phase region without hexagonal phase ($III_1$) is missing from the SLES/CAPB—MD 180—water system with only 1% NaCl. The reason might be that the salt promotes the formation of the rod-like micelles in SLES/CAPB solution and therefore promotes the formation of the hexagonal liquid crystal structure. An other difference is that with 1% NaCl, the $II_1$ phase becomes much smaller while the $II_2$ phase becomes enlarged.

Emulsion With Glycerol

In yet another embodiment, the effect of glycerol on the aqueous-aqueous emulsion was also observed.

As shown in FIG. 5(b), adding 5% glycerol does not really change the phase behavior of the SLES/CAPB (2:1)%—MD 180—water, except that the boundaries of different phase regions move slightly in the direction of the higher surfactant and/or higher MD 180 concentration. Similarly, the boundary between the one-layer and two-layer product also moves to higher surfactant and/or MD 180 concentration side. It is believed glycerin effectively reduces the surface charge density of the surfactant micelles, which enhances the stability of the surfactant—MD 180 solution and delays the phase separation.

Ingredients

Surfactants

Other than the ability to form rod micelles from continuous phase as noted above, the surfactant can be any surfactant which may be selected from the group consisting of anionic surfactants, nonionic surfactants, amphoteric/zwitterionic surfactants, cationic surfactants and mixtures thereof. Preferably, there will be at least one anionic surfactant.

Non-limiting examples of anionic, nonionic or amphoteric surfactants are disclosed in McCutcheon's Detergents and Emulsifiers, North American Edition (1986), published by Allured Publishing Corporation; McCutcheon's Functional materials, North Americas Edition (1992), both of which are incorporated by reference into the subject application.

Cationic surfactants are another useful class of surfactants that can be employed as auxiliary agents. They are particularly useful as additives to enhance skin feel, and provide skin conditioning benefits. One class of cationic surfactants is heterocyclic ammonium salts such as cetyl or stearyl pyridinium chloride, alkyl amidoethyl pyrrylinodium methyl sulfate, lapyrium chloride.

Tetra alkyl ammonium salts is another useful class of cationic surfactants. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides; behenyl dimethy ammonium chloride.

Other types of cationic surfactants that can be employed are the various ethoxylated quaternary amines and ester quats. Examples are PEG-5 stearyl ammonium lactate (e.g., Genamin KSL manufactured by Clarion), PEG-2 coco ammonium chloride, PEG-15 hydrogenated tallow ammonium chloride, PEG 15 stearyl ammonium chloride, dialmitoyl ethyl methyl ammonium chloride, dipalmitoyl hydroxyethyl methyl sulfate, strearyl amidopropyl dimethylamine lactate.

Still other useful cationic surfactants are quaternized hydrolysates of silk, wheat, and keratin proteins.

Other optional components include polyalkylene glycol.

Because the compositions of the invention are personal wash compositions primarily intended for contact with skin during wash, the polyalkylene glycol (whose function is to help keep surfactant dissolved in upper aqueous layers, but which may also function as moisturizing benefit agent) should be an alcohol, glycol or polyether of minimal molecular weight which is not irritating to the skin.

Examples of such include alcohols, particularly polyalkylene oxides having MW 200–6000, preferably 200 to 3000. The polyalkylene glycol can be comprised of ethylene oxide, propylene oxide, butylene oxide or their mixtures either as polymers or copolymers. Specific examples include polyethylene glycols such as PEG 400.

Electrolyte

The compositions of the invention further comprise less than about 30%, preferably less than 5% of an electrolyte.

The electrolyte should preferably not be a chelating electrolyte (which are typically poor in biodegradability).

Typically, the electrolyte should be a salt of a sulphate, bisulfate, carbonate, bicarbonate, phosphate, etc. Examples include sodium, potassium sulphate and ammonium sulphate.

Aqueous solubility of the salt should exceed 30% wt. to volume at 0° C. such that it may be observed that mineral salts will generally be more preferred than organic salts which typically have much lower solubility.

In addition to the ingredients noted above, the compositions of the invention may contain hydrotropes including but not limited to short chain monohydric or dihydric alcohols, xylene sulphonate and hexylene glycol whose purpose is to avoid the formation of liquid crystal phases resulting from the separation of the surfactant material into the upper phase hence increasing its apparent concentration.

Optionals

In addition to the ingredients noted above, the compositions of the invention may contain a variety of optional ingredients such as set forth below:

The compositions may comprise benefit agents. Benefit agent may be any material that has potential to provide an effect on, for example, the skin.

The benefit agent may be water insoluble material that can protect, moisturize or condition the skin upon deposition from compositions of invention. These may include silicon oils and gums, fats and oils, waxes, hydrocarbons (e.g., petrolatum), higher fatty acids and esters, vitamins, sunscreens. They may include any of the agents, for example, mentioned at column 8, line 31 to column 9, line 13 of U.S. Pat. No. 5,759,969, hereby incorporated by reference into the subject application.

The benefit agent may also be a water soluble material such as glycerin, enzyme and α- or β-hydroxy acid either alone or entrapped in an oily benefit agent.

The benefit agent may be found in either the upper or the lower layer depending on its solubility and partition coefficient, for example, oil may partition into the upper layer while more water soluble agents (e.g., α-hydroxyacids) may go into the lower.

The compositions may comprise perfumes, sequestering agents such as EDTA EHDP in amounts 0.01 to 1%, preferably 0.01 to 0.05%; coloring agents, opacifiers and pearlizers such as zinc stearate, magnesium stearate, TiO2, EGMS (ethylene glycol monostrearate) or styrene/acrylate copolymers.

The compositions may further comprise antimicrobials such as 2-hydroxy 4,2'4' trichlorodiphenylether (DP300), 3,4,4'-trichlorocarbanilide, essential oils and preservatives such as dimethyl hydantoin (Glydant XL 1000), parabens, sorbic acid etc.

The compositions may also comprise coconut acyl mono or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used including Quatrisoft LM-200 Polyquaternium-24, Merquat Plus 3330-Polyquaternium 39; and Jaguar® type conditioners.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Materials & Methods

Materials

Sodium Laurethethersulfate (SLES 2EO) was purchased from Stepan. Cocoamidopropyl Betaine (CAPB) was purchased from Goldschmidt. Polydextrose (Maltodextran) of molecular weight 1000 (MD 180) was supplied by Grain Processing.

Formulation Preparation

All ingredients were well mixed, and then were heated for one hour at 60° C. to dissolve solid materials. The samples were then allowed to cool to room temperature. Once the sample reached equilibrium at room temperature, it was mixed by shaking, and visual observations were made. Based on total weights of all of the ingredients, including surfactant, salt and saccharides, weight percentages were calculated to get exact the formulation.

Viscosity & Product Appearance

Formulations were screened for viscosity profiles using a Haake rheometer Specifically, the viscosity measurement of the formulation was performed using HAAKE RV 20 Roto-Visco Rheometer at 20° C. SV1 cup and bob were used for the measurement as the viscosity of the sample is relatively high. The results were recorded as viscosity in mPas (cpa) at the shear rates of 1/sec, 10/sec and 100/sec respectively. Formulations were also observed for any discoloration or re-crystallization of saccharides at room temperature over time.

Microscopy

Olympus BH-2 microscopy was used to observe the microstructure of the sample at room temperature. Polarized light was used to determine the birefringence of the sample as an indication of the existence of the hexagonal and lamellar phase.

Particle Size Measurement

Brook Haven Instruments BI-90 particle size was used to measure the average size of the disperse phase in the aqueous-aqueous emulsion samples.

Gas Chromatography (GC) Analysis of Glycerol

High temperature gas chromatography (GC) was used to analyze the glycerol concentration in the top and bottom layer of the bi-phasic sample. Specifically, the GC analysis was performed on a Hewlett-Packard Model 5890 gas chromatograph fitted with a capillary split/splitless inlet system in the split mode, flame ionization detector, and model 7673 auto sampler. A 10 m×0.32 mm i.d. fused silica capillary column with a 0.1 μm SIM-DIST CB coating supplied by Chrompak. The carrier gas flow was 50 ml/min, with a column flo or 3.5 ml/min 6.1 psi at 50° C. The initial column temperature was 50° C. And the temperature was increased at a rate of 15° C. per minute to reach a final temperature of 375° C. The inlet temperature was 350° C. and the detector temperature was 385° C.

A known quantity of the to player or the bottom layer of a biphasic sample was accurately weighted into a 100-ml volumetric flask, and diluted to volume with methanol. A 1-ml aliquot was transferred to a 2-ml septum vial and the solvent was evaporated by warming the sample at 50° C. which applying a gentle flow of nitrogen for about an hour. After solvent evaporation, the glycerol was silylated by adding 250 µL pyridine and 250 µL bis-trimethylsilytriflouroacetamide (BSTFA) to the septum vial, and heating the sealed vial to 75° C. for 30 minutes. This solution is thus ready for the GC analysis using the instrument stated above. In the stated condition, the silylated glycerin elutes at approximately 4.4 min. The peak area around that retention times used to determine the quantity of the glycerin in the sample.

EXAMPLE 1

SLES/CAPB (2:1)—MD180—Water

Depending on the composition, the surfactant/MD 180 formulation can be an isotropic clear solution, or a cloudy solution. At higher surfactant/MD 180 concentration, samples can separate into two layers, as indicated in FIG. 1(a). The commonly used term "biphasic" usually implies that the product has two visible layers. It was observed from a dye partition experiment in which almost all the dyes partition to the top layer that the bi-phasic formulations typically have a surfactant poor/MD 180 rich bottom layer. The top layer of a two-layer formulation can be clear (for one-phase), cloudy (for two-phase of solutions), or opaque (hexagonal crystal in solution), depending on the phase structures. It can be one phase (a surfactant/MD 180 water solution), or two-phase without liquid crystal (a surfactant rich/MD 180 poor water solution; and a surfactant/MD 180 water solution), or two-phase with liquid crystal (a surfactant rich/MD 180 poor water solution+hexagonal phase).

As indicated by the phase diagram shown in FIG. 1(b), SLES/CAPB (2:1)—MD 180—water system exhibits a rich phase behavior. At low surfactant concentration and low MD 180 concentration, one phase region of SLES/CAPB (2:1)+MD 180 water solution (denoted as $I_1$) exists. As the MD 180 or surfactant concentration increases, phase separation occurs. Two two-phase regions exist on the phase diagram, a mixture of a surfactant/MD 180 solution with a MD 180 rich/surfactant poor solution (denoted as $II_1$), or a mixture of a surfactant rich/MD 180 poor solution with a surfactant/MD 180 solution (denoted as $II_2$). As the surfactant and/or MD 180 concentrations keep on increasing, a three-phase region (denoted as $III_1$), which is a mixture of a surfactant rich/MD 180 poor solution, a surfactant/MD 180 solution and a MD 180 rich/surfactant poor solution, is formed. After that, the increase of MD 180 and/or surfactant concentration leads to another three-phase region ($III_2$), formed by surfactant hexagonal liquid crystal phase, surfactant rich/MD 180 poor phase and a MD 180 rich/surfactant poor phase. It is also noted from the phase diagram that along the SLES/CAPB (2:1) concentration axis, at the low MD 180 concentration region, there is a one-phase region (denoted as I), which is surfactant hexagonal liquid crystal phase, as well as a two-phase region (denoted as II), which is a mixture of surfactant hexagonal liquid crystal phase and a surfactant water solution. The schematics of the evolution of the phase behavior upon the increase of surfactant and/or MD 180 concentration are shown in FIG. 2.

It is also interesting to note that there are two two-phase regions in the phase diagram shown in FIG. 1(b) that may not separate into two layers. Therefore, we may have stable aqueous-aqueous emulsion phases. These are examples of the stable aqueous-aqueous regions claimed in the subject invention. While the formation of aqueous-aqueous two-phase system itself is generally known and relatively easy to achieve, stabilizing a water-in-water emulsion with two different solutes enriching the two phases is not easily achieved. In the aqueous-aqueous emulsion that is explored here, both dispersed and continuous phases are water rich and no other water immiscible solvent is required in the current system. Upon the addition of Maltodextrin into the surfactant water solution, the shape of the surfactant micelle changes from sphere to rod and phase separation happens. The continuous phase formed by rod-like surfactant micelles exhibits a high viscosity where the coalescence of the dispersed phase is greatly reduced and the aqueous/aqueous emulsion is stable.

EXAMPLE 2

System with Salt

The phase diagram of SLES/CAPB (2:1)—MD 180—water with 1% NaCl at room temperature is shown in FIG. 4(b). It is found that at low surfactant and/or low MD 180 concentration, an isotropic solution phase exists. With the increase of the surfactant and/or MD 180 concentration, two two-phase regions are encountered, similar to the SLES/CAPB (2:1)—MD 180—water without NaCl (Example 1). Further increases of the surfactant and/or MD 180 concentration result in the formation of a three-phase region, which is the mixture of the surfactant hexagonal phase, a surfactant rich/MD 180 poor solution, and a surfactant poor/MD 180 rich solution phase.

The discontinuous line in FIG. 4(a) is the boundary that the formulation starts to separate into two layers. For biphasic product of SLES/CAPB—MD 180 with 1% NaCl, the bottom layer is the surfactant poor/MD 180 rich solution. The top layer can be a clear one phase solution (a surfactant+MD 180 water solution), or an opaque two-phase mixture with liquid crystal (a surfactant rich/MD 180 poor water solution+hexagonal phase).

Comparing the phase diagrams of SLES/CAPB—MD 180—water systems with and without NaCl, it is found that the three-phase region without hexagonal phase ($III_1$) is missing from the SLES/CAPB—MD 180—water system with only 1% NaCl. The reason might be that NaCl promotes the formation of the rod-like micelles in SLES/CAPB solution and therefore promotes the formation of the hexagonal liquid crystal structure. Another difference is that with 1% NaCl, the $II_1$ phase becomes much smaller while the $II_2$ phase becomes enlarged.

EXAMPLE 3

SLES/CAPB (2:1)—MD 180—Water with 5% Glycerol

Glycerol is an important benefit agent in personal wash product. As shown in FIG. 5(b), adding 5% glycerol does not really change the phase behavior of the SLES/CAPB (2:1)%—MD 180—water, except that the boundaries of different phase regions move slightly in the direction of the higher surfactant and/or higher MD 180 concentration. Similarly, the boundary between the one-layer and two-layer product also moves to higher surfactant and/or MD 180 concentration side. It is believed that glycerin effectively reduces the surface charge density of the surfactant micelles, which enhances the stability of the surfactant—MD 180 solution and delays the phase separation.

EXAMPLE 4

Rheology experiments were performed to examine the phase separation mechanism. As shown in FIG. 6(a), at a constant surfactant concentration (e.g., 10%), with an increasing MD 180 concentration, the viscosity at shear rate 10 s$^{-1}$ remains low at the isotropic $I_1$ region. However, the viscosity starts to increase dramatically as the MD 180 concentration approaches the phase separation boundary. This increase in viscosity is an indication of the formation of the rod-like micelles in the solution. From FIG. 6(b), it can be seen that the phase separation happens as indicated by increase of particle size. By comparing 6(a) and 6(b), this phase separation occurs at the concentration range that rod-like micelles which form. The same rheology behavior was generally observed along phase separation boundary for all the surfactant concentrations examined. Therefore, based on these observations, it might be hypothesized that with the addition of MD 180 and the decrease of the water content in the system, surfactant aggregates change shape from spherical to rod. And due to the high efficiency of the rod-like micelle in terms of causing depletion induced phase separation, the surfactant/MD 180/water mixture separated into two phases as a consequence.

EXAMPLE 5

Effect of Additives on Phase Boundary

In FIG. 7, the phase separation boundary is shown on a 2D plot (surfactant concentration vs. MD 180 concentration), for SLES/CAPB (2:1)—MD 180—water systems with/without additives. It was found that adding NaCl into the SLES/CAPB (2:1)—MD 180—water formulation shifts the phase separation boundary to the lower surfactant concentration and lower MD 180 concentration side, which means that the phase separation is promoted by addition of electrolyte such as NaCl. It is known that electrolytes promote the formation of the rod-like micelles in surfactant system such as SLES/CAPB. As discussed in the previous paragraph, since the phase separation in SLES/CAPB (2:1)—MD 180—water formulation is a result of a depletion induced phenomena triggered by the formation of rod-like micelle, additives such as NaCl will lead to a phase separation which happens at lower surfactant and/or MD 180 concentrations.

It is also observed from FIG. 7 that the phase separation boundary moved to higher surfactant and/or higher MD 180 concentration side with the addition of 5% glycerol. It is believed that the addition of glycerol into the surfactant solution will decrease the surface charge of a surfactant micelle, which results in a higher free volume for MD 180 molecules and therefore a more stable surfactant—MD 180 solution, similar to the effects of counter ions.

EXAMPLE 6

Dilution Thickening

The concept of dilution thickening describes a phenomenon where the formulation thickens upon dilution with solvent, usually water. Therefore, the formulation is thin enough to get into and out of the container, but becomes sufficiently thick to retain on the hand or skin during application when water is added. It was found in this study that the SLES/CAPB (2:1)—MD 180 formulations exhibit this dilution thickening property. As shown in Table 1, for all the chosen formulations, samples diluted at the ratio of 2:1 (original sample to water) have higher viscosity compared to the original formulation. Also as shown in FIG. 8, the original SLES/CAPB (2:1)—MD 180 sample (for example, SLES/CAPB (2:1) 20%, MD 180 50%) starts at relatively low viscosity. Upon dilution, the viscosity increases to reach a maximum around 3 to 1 dilution ratio. With further dilution, the viscosity decreases. Therefore, SLES/CAPB (2:1)-MD 180 formulation with proper composition (as the example shown in FIG. 8) can be thin enough to be pourable, but will be thick enough to prevent running during wash when a controlled amount of water is added. With further addition of water during rinsing, the diluted formulation will be thin again for rapid rinsing.

TABLE 1

Comparison of the viscosity of the SLES/CAPB (2:1) - MD 180 samples before and after dilution.

| Sample | | | Original | | | 2:1 Dilution | | |
|---|---|---|---|---|---|---|---|---|
| Surf % | MD % | glycerol % | 1 s-1 | 10 s-1 | 100 s-1 | 1 s-1 | 10 s-1 | 100 s-1 |
| 10 | 60 | | 12,230 | 8,300 | 3,490 | 55,220 | 10,560 | 1,069 |
| 15 | 50 | | 11,600 | 4,400 | 2,700 | 171,460 | 13,480 | 1,880 |
| 20 | 50 | | 37,600 | 12,350 | 3,800 | 221,678 | 16,480 | 2,230 |
| 25 | 40 | | 25,634 | 7,933 | 21 | 551,097 | 53,360 | 6,220 |
| 30 | 40 | | 27,088 | 5,849 | 520 | 204,650 | 31,754 | 3,360 |
| 20 | 40 | 5 | 11,435 | 6,848 | 1,315 | 193,037 | 17,196 | 2,065 |

The mechanism of the dilution thickening phenomenon observed in SLES/CAPB (2:1)—MD 180 formulation may be explained from the phase behavior. For any multi-phase formulation, the original formulation exhibits relatively low viscosity due to the existence of the disperse phase. The viscosity of the formulation can be low enough that the disperse phase separates from the continuous phase to form a two-layer product (bi-phasic). Upon dilution, the sample approaches the isotropic solution phase (two-phase to one phase boundary), and viscosity increases due to the existence of the rod-like surfactant micelles and the decreasing amount of the dispersed phase. The viscosity will reach its maximum at the boundary between the isotropic phase. Further dilution with water breaks the rod-like micelle into spherical micelle, which leads to water-like viscosity. This dilution thickening phenomenon happens within a wide range of surfactant and polysaccharide concentrations and will happen with/without salt.

The invention claimed is:
1. A stable, aqueous-aqueous emulsion comprising
(1) a dispersed aqueous phase comprising a molecule or combination of molecules meeting the following criteria:

(a) water solubility of greater than 5%; and
(b) MW>about 200 and <about 200,000; and
(2) a continuous phase comprising surfactant or surfactant system having micelles in rod-like shape,
wherein rod-like is defined by a surfactant parameter of surfactant or surfactants forming the micelle, Ns, of about $\frac{1}{3}$–$\frac{1}{2}$, where Ns is defined by the equation:

$$Ns = V/la_o$$

where V=volume of the hydrophobic portion of the surfactant volume;
 l=the length of the hydrocarbon claims of the surfactant; and
 $a_o$=effective area for head group;
wherein the molecules in the dispersed phase are selected from the group consisting of maltodextrins having MW of about 500 to 5000; PVP having MW of about 7000; dextran having MW of about 70,000; PEG having MW of about 1000, and mixtures thereof.

2. An emulsion according to claim 1, wherein molecule or combination of molecules in dispersed phase has solubility in water>10%.

3. An emulsion according to claim 1, wherein molecule or combination of molecules in dispersed phase has solubility in water>15%.

4. An emulsion according to claim 1, wherein molecule or combination of molecules in dispersed phase has MW>250 and <200,000.

5. An emulsion according to claim 1, wherein molecule or combination of molecules in dispersed phase has MW>200 and <195,000.

6. An emulsion according to claim 1, wherein surfactant system of continuous phase comprises alkali metal ether sulfate and cocoamidopropyl betaine.

7. An emulsion according to claim 1, wherein the ratio of alkali metal ether sulfate to betaine is about 2:1.

8. An emulsion according to claim 1, wherein the surfactant system of continuous phase comprises a surfactant blend comprising anionic and cocomonoethanolamide (CMEA) in combination with betaine.

9. An emulsion according to claim 1, wherein the blend is used in ratio of alkali metal ether sulfate to betaine of about 4:1.

10. An emulsion according to claim 1, additionally comprising salt.

11. An emulsion according to claim 1, additionally comprising glycerin.

12. A process for forming a stable aqueous-aqueous emulsion which process comprises adding to surfactant or surfactant system having surfactant parameter of the surfactant or surfactants, Ns, of about $\frac{1}{3}$–$\frac{1}{2}$, wherein Ns is defined by the equation:

$$Ns = V/la_o$$

where V=volume of the hydrophobic portion of the surfactant volume;
 l=the length of the hydrocarbon claims of the surfactant; and
 $a_o$=effective area for head group,
a molecule meeting the following criteria:
(a) water solubility of greater than 5%; and
(b) MW>about 200 and <about 200,000;
wherein said molecule is selected from the group consisting of maltodextrins having MW of about 500 to 5000; PVP having MW of about 7000; dextran having MW of about 70,000; PEG having MW of about 1000, and mixtures thereof.

* * * * *